(12) United States Patent
Wang

(10) Patent No.: US 12,011,230 B2
(45) Date of Patent: Jun. 18, 2024

(54) CALIBRATION METHOD AND DEVICE FOR DENTAL IMPLANT NAVIGATION SURGERY, AND TRACKING METHOD AND DEVICE FOR DENTAL IMPLANT NAVIGATION SURGERY

(71) Applicant: BEIJING YAKEBOT TECHNOLOGY CO., LTD, Beijing (CN)

(72) Inventor: Lifeng Wang, Beijing (CN)

(73) Assignee: BEIJING YAKEBOT TECHNOLOGY CO., LTD. (CN)

( * ) Notice: Subject to any disclaimer, the term of this patent is extended or adjusted under 35 U.S.C. 154(b) by 547 days.

(21) Appl. No.: 17/418,128

(22) PCT Filed: May 6, 2019

(86) PCT No.: PCT/CN2019/085676
§ 371 (c)(1),
(2) Date: Jun. 24, 2021

(87) PCT Pub. No.: WO2020/133868
PCT Pub. Date: Jul. 2, 2020

(65) Prior Publication Data
US 2022/0054200 A1    Feb. 24, 2022

(30) Foreign Application Priority Data
Dec. 26, 2018  (CN) .......................... 201811602134.5

(51) Int. Cl.
*A61B 34/20*  (2016.01)
*A61B 90/00*  (2016.01)
(Continued)

(52) U.S. Cl.
CPC .............. *A61B 34/20* (2016.02); *A61B 90/39* (2016.02); *A61C 8/0089* (2013.01); *G06T 7/30* (2017.01);
(Continued)

(58) Field of Classification Search
CPC ................... A61B 34/20; A61B 90/39; A61B 2034/2055; A61B 2090/3937;
(Continued)

(56) References Cited

U.S. PATENT DOCUMENTS 9,561,019 B2 * 2/2017 Mihailescu ............ A61B 5/064
2005/0163342 A1  7/2005 Persky
2014/0071258 A1  3/2014 Gandyra
(Continued)

FOREIGN PATENT DOCUMENTS

CN    103251457 A    8/2013
CN    107440797 A    12/2017
(Continued)

OTHER PUBLICATIONS

International Search Report for corresponding International application No. PCT/CN2019/085676; dated Sep. 29, 2019 (2 bages).
(Continued)

*Primary Examiner* — Brandon J Miller
(74) *Attorney, Agent, or Firm* — Mendelsohn Dunleavy,P.C.

(57) ABSTRACT

Embodiments of the present application provide a calibration method and device for dental implant navigation surgery, and a tracking method and device for dental implant navigation surgery. The calibration method comprises: (110) obtaining a position of a scanning area (304) relative to a second visual marker (306) based on a spatial position of a first visual marker (305) disposed on a scanning device (302), a spatial position of the second visual marker (306) disposed on a surgical area (303), and a scanning position of
(Continued)

the scanning area (304) obtained by scanning with the scanning device (302); and (120) registering the position of the scanning area (304) relative to the second visual marker (306) with a three-dimensional scene to obtain a transformation matrix, and applying the transformation matrix to the tracking of a surgical instrument. Therefore, the position change of a surgical instrument may be reflected in real time in the three-dimensional scene without implanting a marker point into the body of a patient, even if the patient's head moves during the surgery, thereby accurately tracking the surgical instrument in real time.

18 Claims, 3 Drawing Sheets

(51) Int. Cl.
*A61C 8/00* (2006.01)
*G06T 7/30* (2017.01)
*G06T 7/70* (2017.01)

(52) U.S. Cl.
CPC ........ *G06T 7/70* (2017.01); *A61B 2034/2055* (2016.02); *A61B 2090/3937* (2016.02); *A61B 2560/0223* (2013.01)

(58) Field of Classification Search
CPC ............. A61B 2560/0223; A61B 2017/00725; A61B 2090/3983; A61B 34/10; A61B 90/36; A61B 2034/105; A61B 2034/107; A61B 2034/108; A61B 2034/2046; A61B 2034/2068; A61B 2090/364; A61C 8/0089; A61C 9/0046; A61C 9/0053; A61C 1/084; G06T 7/30; G06T 7/70
See application file for complete search history.

(56) References Cited

U.S. PATENT DOCUMENTS

2014/0135746 A1  5/2014  Schoepp
2018/0153626 A1  6/2018  Yang et al.

FOREIGN PATENT DOCUMENTS

| CN | 107582193 A | 1/2018 | |
|---|---|---|---|
| CN | 107898499 A | 4/2018 | |
| CN | 108056819 A | 5/2018 | |
| CN | 108705536 A | 10/2018 | |
| CN | 109077822 A | 12/2018 | |
| CN | 109692050 A | 4/2019 | |
| JP | 2007-209531 A | 8/2007 | |
| JP | 2010-259497 A | 11/2010 | |
| JP | 6238330 B1 | 11/2017 | |
| KR | 10-2018-0019402 A | 2/2018 | |
| WO | WO-2014170340 A1 * | 10/2014 | ............. A61B 19/50 |
| WO | WO-2018127501 A1 * | 7/2018 | ............. A61B 34/20 |
| WO | 2018155894 A1 | 8/2018 | |

OTHER PUBLICATIONS

First Office Action for corresponding Chinese application No. 201811602134.5; dated Nov. 27, 2019 (16 pages) Machine Translation.

Extended European Search Report for corresponding European application No. 19902087.6; dated Jan. 21, 2022 (7 pages).

Notice of Reasons for Refusal for corresponding Japanese application No. 2021-537712; dated Jun. 12, 2022 (11 pages) Machine Translation.

Reasons for Refusal for corresponding Korean application No. 10-2021-7015921; dated Aug. 22, 2022 (15 pages) Machine Translation.

Reasons for Refusal for corresponding Korean application No. 10-2021-7015921; dated Feb. 27, 2023 (16 pages) Machine Translation.

Notice of Final Rejection for corresponding Korean application No. 10-2021-7015921; dated Aug. 28, 2023 (11 pages) Machine Translation.

Notice of Final Rejection for corresponding Korean application No. 10-2021-7015921; dated Jan. 24, 2024 (12 pages) Machine Translation.

* cited by examiner

CALIBRATION METHOD AND DEVICE FOR DENTAL IMPLANT NAVIGATION SURGERY, AND TRACKING METHOD AND DEVICE FOR DENTAL IMPLANT NAVIGATION SURGERY

CROSS-REFERENCE TO RELATED APPLICATION

The present application claims priority to Chinese patent application No. 201811602134.5 filed on Dec. 26, 2018, entitled "Calibration Method and Device for Dental Implant Navigation Surgery, and Tracking Method and Device for Dental Implant Navigation Surgery," which is hereby incorporated by reference in its entirety.

FIELD OF TECHNOLOGY

The embodiments of the present application relate to the technical field of medical treatment, in particular to a calibration method and a calibration device for dental implant navigation surgery, and a tracking method and a tracking device for dental implant navigation surgery.

BACKGROUND

In recent years, with the promotion of oral implant technology in the clinic and the improvement of people's demand for oral health, more and more patients choose implant restoration treatment for missing teeth. An oral implant surgery is a precise operation under local anesthesia in a narrow space. The failure rate of the implant surgery is high due to factors such as indirect vision environment of the oral cavity, narrow operating space and lack of experience of dentists.

With the development of computer technology, surgical navigation, possessing the advantages of precision, flexibility and minimally invasiveness, has brought revolutionary changes to surgeries and also provided a direction for the further development of stomatology. At present, the basic method of oral implant navigation technology developed at home and abroad is to reconstruct the three-dimensional image of a patient's oral cavity based on CT scan data, and to plan an ideal three-dimensional position of an implant in advance in an auxiliary design software. During the surgery, optical or electromagnetic navigation instruments are adopted to track spatial positions of surgical instruments in real time, and an implant cavity is prepared according to the ideal position, angle and depth determined in advance, and then the implant is implanted.

A key step in the above-mentioned oral implant navigation surgery is to determine the mapping relationship between a virtual image space and a visual space, so as to track the spatial positions of the surgical instruments in real time. At present, the registration method of marker points is often used in clinic, that is, the mapping relationship between the two spaces is established by determining the mapping relationship between the marker points on the medical image and the corresponding marker points on the human body. The marker point may be either an anatomical marker point of the jaw or tooth, or an artificial marker point having small volume. However, if the anatomical marker points are used for registration, it will bring about the problem of low registration precision: and if the artificial marker points are used for registration, the artificial marker points need to be implanted into the patient's alveolar process or jaw, which may cause unnecessary trauma or even infection.

BRIEF SUMMARY

Embodiments of the present application provide a calibration method and a method device for dental implant navigation surgery, and a tracking method and a tracking device for dental implant navigation surgery, so as to solve the problem of low registration accuracy or unnecessary trauma to the patient in the setting of marker points during the tracking of the traditional dental implant surgery instruments.

In a first aspect, an embodiment of the present application provides a calibration method for dental implant navigation surgery, including:

obtaining a position of a scanning area relative to a second visual marker based on a spatial position of a first visual marker disposed on a scanning device, a spatial position of the second visual marker disposed on a surgical area, and a scanning position of the scanning area obtained by scanning with the scanning device; and registering the position of the scanning area relative to the second visual marker with a three-dimensional scene to obtain a transformation matrix.

In a second aspect, an embodiment of the present application provides a tracking method for dental implant navigation surgery, including:

capturing a spatial position of a second visual marker disposed on a surgical area and a spatial position of a third visual marker disposed on a surgical instrument; and updating the position of the surgical instrument in a three-dimensional scene based on the spatial position of the second visual marker, the spatial position of the third visual marker, and a transformation matrix:

wherein the transformation matrix is obtained based on the calibration method for dental implant navigation surgery provided in the first aspect.

In a third aspect, an embodiment of the present application provides a calibration device for dental implant navigation surgery, including:

a relative position acquirer, configured to obtain a position of a scanning area relative to a second visual marker based on a spatial position of a first visual marker disposed on a scanning device, a spatial position of the second visual marker disposed on a surgical area, and a scanning position of the scanning area obtained by scanning with the scanning device; and a transformation matrix acquirer, configured to register the position of the scanning area relative to the second visual marker with a three-dimensional scene to obtain a transformation matrix.

In a fourth aspect, an embodiment of the present application provides a tracking device for dental implant navigation surgery, including:

a capturer, configured to capture a spatial position of a second visual marker disposed on a surgical area and a spatial position of a third visual marker disposed on a surgical instrument; and a tracker, configured to update the position of the surgical instrument in a three-dimensional scene based on the spatial position of the second visual marker, the spatial position of the third visual marker, and a transformation matrix:

wherein the transformation matrix is obtained based on the calibration method for dental implant navigation surgery provided in the first aspect.

In a fifth aspect, an embodiment of the present application provides an electronic apparatus, including a processor, a communication interface, a memory, and a bus, wherein the processor, the communication interface, and the memory communicate with each other through the bus, and the processor may call logic instructions in the memory to perform steps of the method provided in the first aspect or the second aspect.

In a sixth aspect, an embodiment of the present application provides a non-transitory computer readable storage medium, in which computer programs are stored, where steps of the method provided in the first aspect or the second aspect are implemented when the computer programs are executed by a processor.

The embodiments of the present application provide a calibration method and a calibration device for dental implant navigation surgery, and a tracking method and a tracking device for dental implant navigation surgery. Through the second visual marker disposed on the surgical area and the first visual marker disposed on the scanning device, the transformation matrix is obtained and then is applied to the tracking of surgical instruments. Therefore, the position change of a surgical instrument may be reflected in real time in the three-dimensional scene without implanting a marker point into the body of a patient, even if the patient's head moves during the surgery, thereby accurately tracking the surgical instrument in real time.

BRIEF DESCRIPTION OF THE DRAWINGS

In order to illustrate the technical solutions of the embodiments in the present application or the prior art more clearly, drawings needed in the description of the embodiments or the prior art will be briefly introduced below. Obviously, the drawings in the following description show some embodiments of the present application. For those of ordinary skill in the art, other drawings can be obtained based on these drawings without creative work.

Figure 1:
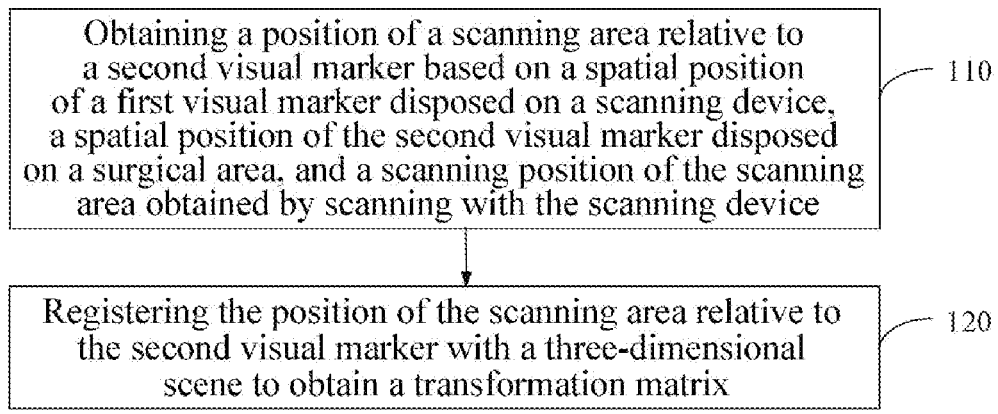
FIG. 1 is a schematic flowchart of a calibration method for dental implant navigation surgery according to an embodiment of the present application.

REFERENCE NUMERALS 301 optical navigator 302 scanning device
303 surgical area 304 scanning area
305 first visual marker 306 second visual marker

DETAILED DESCRIPTION

In order to illustrate the objectives, technical solutions and advantages of the embodiments of the present application more clearly, the technical solutions in the embodiments of the present application will be described clearly and completely in conjunction with the accompanying drawings in the embodiments of the present application. Obviously, the described embodiments are part of the embodiments of the present application, rather than all of the embodiments. All other embodiments obtained by a person of ordinary skill in the art based on the embodiments of the present application without any creative effort fall within the protection scope of the present application.

In a traditional oral implant navigation surgery, the mapping relationship between the virtual image space and the visual space is determined by a marker point registration method, so as to tracking the spatial position of a surgical instrument in real time. When anatomical marker points are used for registration, there is a problem of low registration accuracy; and when artificial marker points are used for registration, the artificial marker points need to be implanted into a patient's alveolar process or jaw, which may cause unnecessary trauma to the patient or even infection. In view of the above-mentioned problems, an embodiment of the present application provides a calibration method for dental implant navigation surgery. FIG. 1 is a schematic flowchart of a calibration method for dental implant navigation surgery according to an embodiment of the present application. As shown in FIG. 1, the calibration method includes:

step 110, obtaining a position of a scanning area relative to a second visual marker based on a spatial position of a first visual marker disposed on a scanning device, a spatial position of the second visual marker disposed on a surgical area, and a scanning position of the scanning area obtained by scanning with the scanning device.

In an embodiment, before dental implant surgical instruments are tracked, it is necessary to obtain the transformation matrix and construct the transformation relationship between space coordinates and three-dimensional coordinates. When the transformation matrix is obtained, a scanning device is used to scan the surgical area. Here, the surgical area refers to a relevant area where medical treatment is required during a dental surgery, such as the patient's oral jaws or teeth, which is not specifically defined by the embodiments of the present application. The scanning device is configured to scan the surgical area and construct the surgical area in a three-dimensional scene. The scanning area obtained by scanning with the scanning device is a part of the surgical area and corresponds to the scanning area in the three-dimensional scene, and the scanning position of the scanning area is a position coordinate relative to the center of the scanning device. Visual markers are markers that may be captured by devices such as vision sensors in real time, and both the first visual marker and the second visual marker are configured to distinguish the positions where the visual markers are disposed. The first visual marker is disposed on the scanning device, while the second visual marker is disposed on the surgical area. The first visual marker is configured to indicate the spatial position of the scanning device, the second visual marker is configured to indicate the spatial position of the surgical area, and the scanning position is configured to characterize the position of the scanning area relative to the scanning device. The position of the scanning area relative to the second visual marker may be obtained by performing spatial coordinate transformation on the spatial position of the first visual marker, the spatial position of the second visual marker, and the scanning position of the scanning area.

Step 120, registering the position of the scanning area relative to the second visual marker with a three-dimensional scene to obtain a transformation matrix.

In an embodiment, by registering the position of the scanning area relative to the second visual marker and the position corresponding to the scanning area in the three-dimensional scene, the transformation relationship from the position relative to the second visual marker to the position in the three-dimensional scene may be obtained, that is, the transformation matrix may be obtained. Any position relative to the second visual marker may be transformed into a position in the three-dimensional scene through the transformation matrix. In addition, because the second visual marker is capable of characterizing the position of the surgical area, the position of the surgical instrument relative to the second visual marker may be transformed through the transformation matrix based on a transformation with the transformation matrix, without being disturbed by the position change of the surgical area during the actual operation. Even if the patient's head moves during the surgery, the position change of the surgical instrument may be reflected in the three-dimensional scene in real time, thereby tracking the surgical instrument in real time.

In the method provided in the embodiment of the present application, through the second visual marker disposed on the surgical area and the first visual marker disposed on the scanning device, the transformation matrix is obtained and then is applied to the tracking of surgical instruments. Therefore, the position change of a surgical instrument may be reflected in real time in the three-dimensional scene without implanting a marker point into the body of a patient, even if the patient's head moves during the surgery, thereby accurately tracking the surgical instrument in real time.

On the basis of the foregoing embodiment, step 110 specifically includes:

111, obtaining a spatial position of the scanning device based on the spatial position of the first visual marker.

In an embodiment, the first visual marker is disposed at any position on the scanning device. The spatial position of the first visual marker may only be configured to characterize the spatial position of the first visual marker setting position on the scanning device, and cannot accurately represent the scanning device, especially the position of the center point of the scanning device. Therefore, after the spatial position of the first visual marker is obtained, the spatial position of the scanning device would be obtained based on the specific position of the first visual marker on the scanning device.

Further, assuming that the spatial position of the first visual marker is represented by a homogeneous matrix $_V^{M1}T$, and the position of the first visual marker relative to the center of the scanning device is represented by a homogeneous matrix $_S^{M1}T$, where S represents a coordinate system of the scanning device, M1 represents a coordinate system of the first visual marker, and V represents a spatial coordinate system. Then, based on the spatial position $_V^{M1}T$ of the first visual marker, and the position $_S^{M1}T$ of the first visual marker relative to the center of the scanning device, the spatial position of the scanning device is obtained as $_V^{S}T = _V^{M1}T \cdot _S^{M1}T^{-1}$.

112, obtaining a spatial position of the scanning area based on the scanning position of the scanning area and the spatial position of the scanning device.

Assuming that the scanning position of the scanning area, that is, the three-dimensional coordinate point relative to the center of the scanning device obtained by the scanning device at a certain moment is $^SP$, the scanning position of the scanning area is transformed to the spatial coordinate system, and the spatial position of the scanning area is obtained as $^VP = _S^{V}T \cdot ^SP$.

113, obtaining the position of the scanning area relative to the second visual marker based on the spatial position of the scanning area and the spatial position of the second visual marker.

Assuming that the spatial position of the second visual marker is $_V^{M2}T$, where M2 represents a coordinate system of the second visual marker. Based on the spatial position $^VP$ of the scanning area and the spatial position $_V^{M2}T$ of the second visual marker, the spatial position of the scanning area is transformed to the coordinate system of the second visual marker, and the position of the scanning area relative to the second visual marker is obtained as $^{M1}P = _V^{M2}T \cdot ^VP$.

On the basis of any one of the foregoing embodiments, step 120 specifically includes: obtaining a position corresponding to the scanning area in the three-dimensional scene based on an iterative closest point (ICP) algorithm: and obtaining the transformation matrix based on the position of the scanning area relative to the second visual marker and the position corresponding to the scanning area in the three-dimensional scene.

In an embodiment, the iterative closest point algorithm is an iterative calculation method that is mainly used for the accurate stitching of depth images in computer vision, which achieves the accurate stitching by minimizing the corresponding points between source data and target data through continuous iteration. In the embodiment of the present application, the position corresponding to the scanning area in the three-dimensional scene is obtained through the iterative closest point algorithm.

Assuming the position of the scanning area relative to the second visual marker is $^{M2}P$, and the corresponding position of the scanning area in the three-dimensional scene is $^{CT}P$, the transformation matrix used to transform the coordinate system of the second visual marker to that of the three-dimensional scene is $_{CT}^{M2}T = ^{M2}P \cdot ^{CT}T^{-1}$, where CT represents the coordinate system of the three-dimensional scene.

Figure 2:
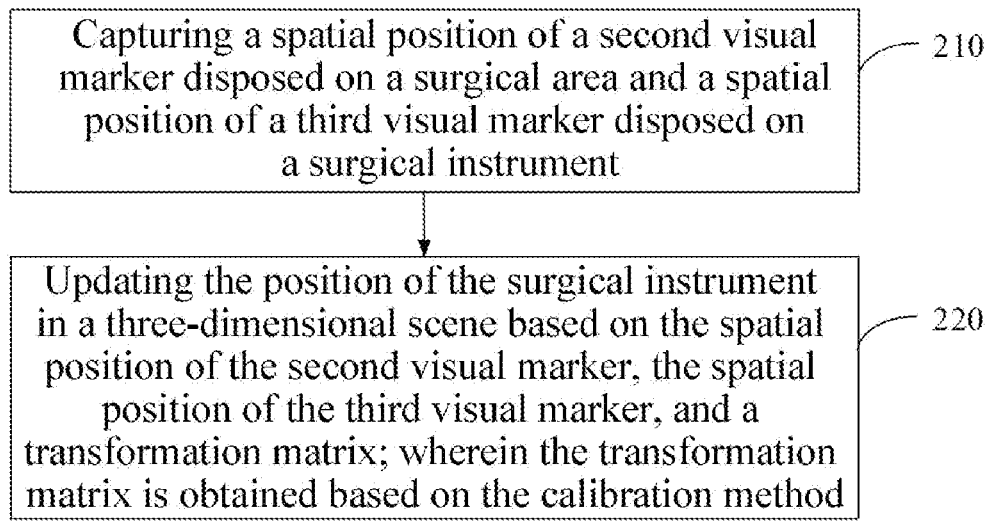
FIG. 2 is a schematic flowchart of a tracking method for dental implant navigation surgery according to an embodiment of the present application.

On the basis of any one of the foregoing embodiments, FIG. 2 is a schematic flowchart of a tracking method for dental implant navigation surgery according to an embodiment of the present application. As shown in FIG. 2, the tracking method includes:

step 210, capturing a spatial position of a second visual marker disposed on a surgical area and a spatial position of a third visual marker disposed on a surgical instrument.

In an embodiment, in the dental implant surgery, visual markers are disposed on the surgical instruments and the surgical area respectively for the navigation of the implant surgery. Here, the surgical instruments refer to medical instruments used in a dental surgery, and the surgical area refers to the relevant area requiring medical treatment during the dental surgery, such as the patient's oral jaws or teeth, which are not specifically defined by the embodiments of the present application. Visual markers are markers that enable devices such as vision sensors to capture location information in real time. The third visual marker and the second visual marker are both configured to distinguish the positions of the visual markers. The third visual marker is disposed on the surgical instrument, the second visual marker is disposed on the surgical area, the third visual marker is configured to indicate the spatial position of the surgical instrument, and the second visual marker is configured to indicate the spatial position of the surgical area.

Step 220: updating the position of the surgical instrument in a three-dimensional scene based on the spatial position of the third visual marker, the spatial position of the second visual marker, and a transformation matrix.

Here, the transformation matrix is obtained based on the calibration method provided in any one of the foregoing embodiments. The transformation matrix is configured to realize the transformation of the spatial position and the position in the three-dimensional scene. For example, based on the spatial position of the third visual marker and the spatial position of the second visual marker, the position of the third visual marker relative to the second visual marker is obtained, and the position of the third visual marker relative to the second visual marker is subsequently transformed to the position of the surgical instrument relative to the surgical area in three-dimensional coordinates based on the transformation matrix, thereby tracking the position of the surgical instrument in real time and guiding the medical personnel to perform the surgery.

In the method provided in the embodiment of the present application, the transformation matrix is applied to the tracking of surgical instruments. Therefore, the position change of a surgical instrument can be reflected in real time in the three-dimensional scene without implanting a marker point into the body of a patient, even if the patient's head moves during the surgery, thereby accurately tracking the surgical instrument in real time.

On the basis of any one of the foregoing embodiments, step 220 specifically includes:

221, obtaining a spatial position of the surgical instrument based on the spatial position of the third visual marker.

In an embodiment, the third visual marker is disposed at any position on the surgical instrument. The spatial position of the third visual marker may only be used to characterize the spatial position of the third visual marker setting position on the surgical instrument, and cannot accurately represent the surgical instrument, especially the position of the center point of the surgical instrument. Therefore, after the spatial position of the third visual marker is obtained, the spatial position of the surgical instrument would be obtained based on the specific position of the third visual marker on the surgical instrument.

Further, assuming that the spatial position of the third visual marker is represented by a homogeneous matrix $_V^{M3}T$, and the position of the third visual marker relative to the center of the surgical instrument is represented by a homogeneous matrix $_R^{M3}T$, where R represents a coordinate system of the surgical instrument, M3 represents a coordinate system of the third visual marker, and V represents a spatial coordinate system. Then, based on the spatial position $M_V^{M3}T$ of the third visual marker, and the position $_R^{M3}T$ of the third visual marker relative to the center of the surgical instrument, the spatial position of the surgical instrument is obtained as $_V^{R}T=_V^{M3}T\cdot_R^{M3}T^{-1}$.

222, obtaining a position of the surgical instrument relative to the second visual marker based on the spatial position of the surgical instrument and the spatial position of the second visual marker.

It is assumed that the spatial position of the second visual marker is $_V^{M2}T$ where M2 represents a coordinate system of the second visual marker. Based on the spatial position $_V^{T}T$ of the surgical instrument and the spatial position $_V^{M2}T$ of the second visual marker, the spatial position of the surgical instrument is transformed to the coordinate system of the second visual marker, and the position of the surgical instrument relative to the second visual marker is obtained as $_{M2}^{R}T=_V^{R}T\cdot_V^{M2}T^{-1}$.

223, updating the position of the surgical instrument in the three-dimensional scene based on the position of the surgical instrument relative to the second visual marker and the transformation matrix.

It is assumed that the transformation matrix is MAT, where CT represents a coordinate system of the three-dimensional scene. The position of the surgical instrument relative to the second visual marker is transformed to the coordinate system of the three-dimensional scene, to obtain the position of the surgical instrument in the three-dimensional scene as $_{CT}^{R}T=_{M2}^{R}T\cdot_{CT}^{M2}T^{-1}$.

Figure 3:
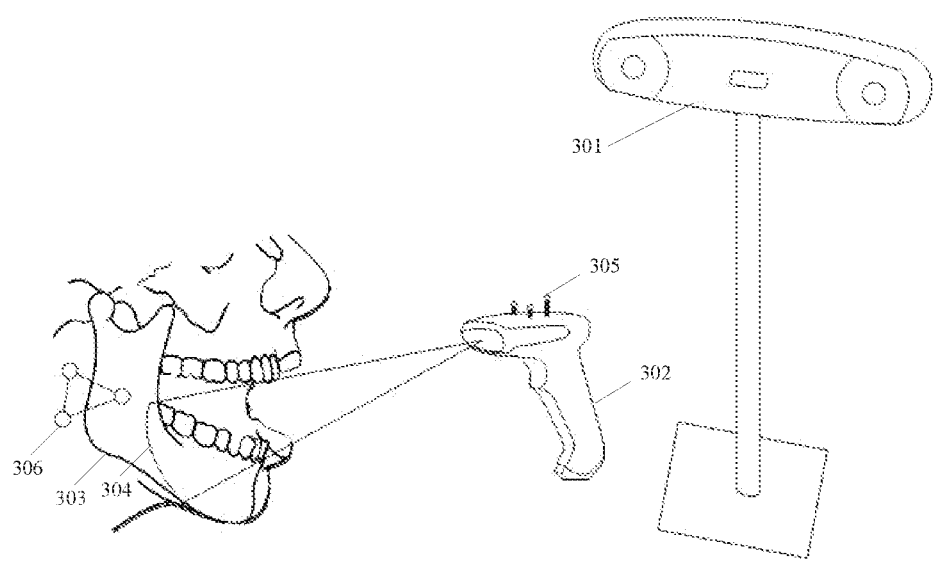
FIG. 3 is a schematic structural diagram of a calibration device for dental implant navigation surgery according to an embodiment of the present application.

On the basis of any one of the foregoing embodiments, FIG. 3 is a schematic structural diagram of a calibration device for dental implant navigation surgery according to an embodiment of the present application. As shown in FIG. 3, before implementing the method of tracking dental implant surgery instrument, the transformation matrix needs to be obtained first. The surgical area 303 of the patient, that is, the jawbone of the patient, is provided thereon with a second visual marker 306. The scanning device 302 is an optical scanner, and is provided thereon with a first visual marker 305. The optical navigator 301 is configured to capture spatial positions of the second visual marker 306 and the first visual marker 305.

On the scanning device 302, the position posture relationship of the first visual marker 305 relative to the optical center of the scanning device 302 has been calibrated and may be represented by a homogeneous matrix $_S^{M1}T$, where S represents a coordinate system of the scanning device 302, and M1 represents a coordinate system of the first visual marker 305. Given the homogeneous matrix $_S^{M1}T$, the relative position of the optical center of the scanning device 302 with respect to the optical navigator 301, that is, the spatial position of the scanning device 302, may be obtained during the scanning process of the scanning device 302. The spatial position of the scanning device 302 is expressed in terms of the homogeneous matrix as $_V^{S}T=_V^{M1}T\cdot_S^{M1}T^{-1}$, where V represents a spatial coordinate system, that is, a coordinate system centered on the optical navigator 301.

The relative positional relationship between the second visual marker 306 and the patient's teeth always remains unchanged. The scanning device 302 with a first visual marker 305 is adopted to scan the patient's oral cavity. During the scanning process, the optical navigator 301 is configured to track the spatial positions of the second visual marker 306 and the first visual marker 305 in real time, and transforms the scanning area on the patient's oral surface obtained by scanning, that is, three-dimensional spatial points, to the coordinate system of the second visual marker 306 for description. The specific method is as follows: the coordinate points of the scanning area 304 acquired by the scanning device 302 are transformed to the visual coordinate system of the optical navigator 301 based on the transformation matrix $_V^{S}T$, that is, the three-dimensional coordinate point $^{S}P$ relative to the optical center of the scanning device 302 acquired at a certain moment in the oral scan is transformed to the visual coordinate system of the optical navigator 301 as $^{V}P=_V^{S}T\cdot^{S}P$; at the same moment, the position posture of the second visual marker 306 under the visual coordinate system of the optical navigator 301 is $_V^{M2}T$, then the three-dimensional scanning point may be transformed to the coordinate system of the second visual marker 306 for description, that is, the position of the scanning area 304 relative to the second visual marker 306 is obtained as $^{M2}P=_V^{M2}T\cdot^{V}P$.

Subsequently, the position $^{M2}P$ of the scanning area 304 relative to the second visual marker 306 is registered with the three-dimensional scene, and the transformation matrix $_{CT}{}^{M2}T={}^{M2}P\cdot{}^{CT}T^{-1}$ is calculated using the iterative closest point algorithm.

After the transformation matrix is obtained, the tracking method for dental implant navigation surgery is performed.

The third visual marker is disposed on the surgical instrument. When tracking the surgical instrument, the optical navigator 301 is configured to track the spatial positions of the third visual marker and the second visual marker 306 in real time. The spatial position of the third visual marker is represented by a homogeneous matrix $_V{}^{M3}T$. On the surgical instrument, the position posture relationship of the third visual marker relative to the center of the surgical instrument has been calibrated and may be represented by a homogeneous matrix $_S{}^{M3}T$; where R represents a coordinate system of the surgical instrument, M3 represents a coordinate system of the third visual marker, and V represents a spatial coordinate system. Then, based on the spatial position $_V{}^{M3}T$ of the third visual marker and the position $_R{}^{M3}T$ of the third visual marker relative to the center of the surgical instrument, the spatial position of the surgical instrument is obtained as $_V{}^{R}T=_V{}^{M3}T\cdot_R{}^{M3}T^{-1}$.

The relative positional relationship between the second visual marker 306 and the patient's teeth always remains unchanged. When tracking the surgical instrument, the optical navigator 301 is configured to track the spatial position of the second visual marker 306 in real time as $_V{}^{M2}T$, where M2 represents a coordinate system of the second visual marker 306. Based on the spatial position $_V{}^{R}T$ of the surgical instrument and the spatial position $_V{}^{M2}T$ of the second visual marker 306, the spatial position of the surgical instrument is transformed to the coordinate system of the second visual marker 306, to obtain the position of the surgical instrument relative to the second visual marker 306 as $_{M2}{}^{R}T=_V{}^{R}T\cdot_V{}^{M2}T^{-1}$. Subsequently, the position of the surgical instrument relative to the second visual marker 306 is transformed to the coordinate system of the three-dimensional scene, and the position of the surgical instrument in the three-dimensional scene is obtained as $_{CT}{}^{R}T=_{M2}{}^{R}T\cdot_{CT}{}^{M2}T^{-1}$.

In the method provided in the embodiment of the present application, through the second visual marker 306 disposed on the surgical area 303 and the first visual marker 305 disposed on the scanning device 302, the transformation matrix is obtained and then is applied to the tracking of surgical instruments. Therefore, the position change of a surgical instrument may be reflected in real time in the three-dimensional scene without implanting a marker point into the body of a patient, even if the patient's head moves during the surgery, thereby accurately tracking the surgical instrument in real time.

Figure 4:
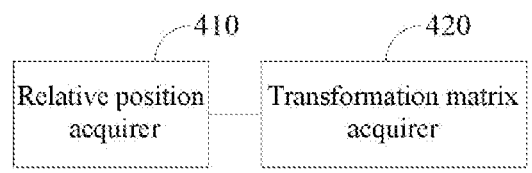
FIG. 4 is a schematic structural diagram of a calibration device for dental implant navigation surgery according to another embodiment of the present application.

On the basis of any one of the foregoing embodiments, FIG. 4 is a schematic structural diagram of a calibration device for dental implant navigation surgery according to another embodiment of the present application. As shown in FIG. 4, provided is a calibration device for dental implant navigation surgery, including a relative position acquirer 410 and a transformation matrix acquirer 420:

wherein the relative position acquirer 410 is configured to obtain a position of a scanning area relative to a second visual marker based on a spatial position of a first visual marker disposed on a scanning device, a spatial position of the second visual marker disposed on a surgical area, and a scanning position of the scanning area obtained by scanning with the scanning device; and the transformation matrix acquirer 420 is configured to register the position of the scanning area relative to the second visual marker with a three-dimensional scene to obtain a transformation matrix.

In the device provided in the embodiment of the present application, through the second visual marker disposed on the surgical area and the first visual marker disposed on the scanning device, the transformation matrix is obtained and then is applied to the tracking of surgical instruments. Therefore, the position change of a surgical instrument can be reflected in real time in the three-dimensional scene without implanting a marker point into the body of a patient, even if the patient's head moves during the surgery, thereby accurately tracking the surgical instrument in real time.

On the basis of any one of the foregoing embodiments, the relative position acquirer 410 includes a device spatial subunit, an area spatial subunit, and an area relative subunit.

The device spatial subunit is configured to obtain the spatial position of the scanning device based on the spatial position of the first visual marker;

the area spatial subunit is configured to obtain the spatial position of the scanning area based on the scanning position of the scanning area and the spatial position of the scanning device; and the area relative subunit is configured to obtain the position of the scanning area relative to the second visual marker based on the spatial position of the scanning area and the spatial position of the second visual marker.

On the basis of any one of the foregoing embodiments, the device spatial subunit is specifically configured to:

obtain the spatial position of the scanning device based on the spatial position of the first visual marker and a position of the first visual marker relative to a center of the scanning device.

On the basis of any one of the foregoing embodiments, the transformation matrix acquirer 420 is configured to:

obtain a position corresponding to the scanning area in the three-dimensional scene based on iterative closest point algorithm; and obtain the transformation matrix based on the position of the scanning area relative to the second visual marker and the position corresponding to the scanning area in the three-dimensional scene.

Figure 5:
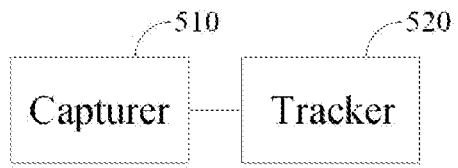
FIG. 5 is a schematic structural diagram of a tracking device for dental implant navigation surgery according to an embodiment of the present application.

On the basis of any one of the foregoing embodiments, FIG. 5 is a schematic structural diagram of a tracking device for dental implant navigation surgery according to an embodiment of the present application. As shown in FIG. 5, provided is a tracking device for dental implant navigation surgery, including a capturer 510 and a tracker 520;

wherein, the capturer 510 is configured to capture a spatial position of a second visual marker disposed on a surgical area and a spatial position of a third visual marker disposed on a surgical instrument: and the tracker 520 is configured to update the position of the surgical instrument in a three-dimensional scene based on the spatial position of the second visual marker, the spatial position of the third visual marker, and a transformation matrix: where the transformation matrix is obtained based on the calibration method of the foregoing embodiments.

In the device provided in the embodiment of the present application, the transformation matrix is applied to the tracking of surgical instruments. Therefore, the position change of a surgical instrument may be reflected in real time in the three-dimensional scene without implanting a marker point into the body of a patient, even if the patient's head moves during the surgery, thereby accurately tracking the surgical instrument in real time.

On the basis of any one of the foregoing embodiments, the tracker 520 specifically includes an instrument spatial subunit, an instrument relative subunit, and an instrument 3D subunit.

The instrument spatial subunit is configured to obtain a spatial position of the surgical instrument based on the spatial position of the third visual marker;

the instrument relative subunit is configured to obtain a position of the surgical instrument relative to the second visual marker based on the spatial position of the surgical instrument and the spatial position of the second visual marker; and the instrument 3D subunit is configured to update the position of the surgical instrument in the three-dimensional scene based on the position of the surgical instrument relative to the second visual marker and the transformation matrix.

Figure 6:
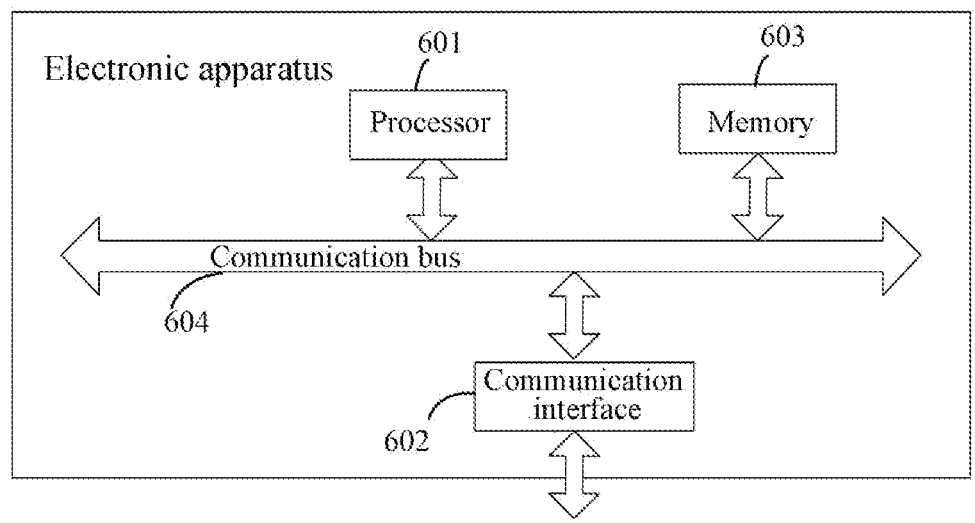
FIG. 6 is a schematic structural diagram of an electronic apparatus according to an embodiment of the present application.

FIG. 6 is a schematic structural diagram of an electronic apparatus according to an embodiment of the present application. As shown in FIG. 6, the electronic apparatus may include: a processor 601, a communication interface 602, a memory 603, and a communication bus 604, where the processor 601, the communication interface 602, and the memory 603 communicate with each other through the communication bus 604. The processor 601 may call computer programs stored in the memory 603 and runnable on the processor 601 to perform the calibration method for dental implant navigation surgery provided by the foregoing embodiments, which includes, for example: obtaining a position of a scanning area relative to a second visual marker based on a spatial position of a first visual marker disposed on a scanning device, a spatial position of the second visual marker disposed on a surgical area, and a scanning position of the scanning area obtained by scanning with the scanning device; and registering the position of the scanning area relative to the second visual marker with a three-dimensional scene to obtain a transformation matrix.

In addition, the processor 601 may also call computer programs stored in the memory 603 and runnable on the processor 601 to perform the tracking method for dental implant navigation surgery provided by the foregoing embodiments, which includes, for example: capturing a spatial position of a second visual marker disposed on a surgical area and a spatial position of a third visual marker disposed on a surgical instrument: and updating the position of the surgical instrument in a three-dimensional scene based on the spatial position of the second visual marker, the spatial position of the third visual marker, and a transformation matrix; where the transformation matrix is obtained based on the calibration method.

In addition, logical instructions of the computer programs in the above-mentioned memory 603 may be implemented in the form of a software functional unit, and may be stored in a computer readable storage medium when sold or used as an independent product. Based on such understanding, the technical solutions of the embodiments of the present application in essential or a part thereof that contributes to the prior art, or a part of the technical solutions can be embodied in the form of software product. The computer software product is stored in a storage medium, and includes several instructions to cause a computer device (which can be a personal computer, server, network device and the like) to perform all or part of the steps of the method described in various embodiments of the present application. The aforementioned storage medium includes: U disk, mobile hard disk, read-only memory (ROM), random access memory (RAM), magnetic disk or compact disk and other medium that can store program codes.

An embodiment of the present application further provides a non-transitory computer readable storage medium, in which computer programs are stored, wherein when the computer programs are executed by a processor, the calibration method for dental implant navigation surgery provided by the above embodiments are implemented, which includes, for example: obtaining a position of a scanning area relative to a second visual marker based on a spatial position of a first visual marker disposed on a scanning device, a spatial position of the second visual marker disposed on a surgical area, and a scanning position of the scanning area obtained by scanning with the scanning device: and registering the position of the scanning area relative to the second visual marker with a three-dimensional scene to obtain a transformation matrix.

An embodiment of the present application further provides a non-transitory computer readable storage medium, in which computer programs are stored, wherein when the computer programs are executed by a processor, the tracking method for dental implant navigation surgery provided by the above embodiments are implemented, which includes, for example: capturing a spatial position of a second visual marker disposed on a surgical area and a spatial position of a third visual marker disposed on a surgical instrument: and updating the position of the surgical instrument in a three-dimensional scene based on the spatial position of the second visual marker, the spatial position of the third visual marker, and a transformation matrix; where the transformation matrix is obtained based on the calibration method.

The above-mentioned device embodiments are merely illustrative, wherein, the units described as separate components may or may not be physically separated, and the components displayed as units may or may not be physical units, that is, they may be located at one place or distributed across multiple network units. Some or all of the modules may be selected according to the actual needs to achieve the purpose of the solutions in the embodiments. Those of ordinary skill in the art can understand and implement them without paying creative labor.

Through the above description of implementations, those of ordinary skill in the art can clearly understand that the various embodiments can be implemented by means of software and necessary general hardware platform, and of course, by means of hardware. Based on such understanding, the above technical solutions in essential or a part thereof that contributes to the prior art can be embodied in the form of software product. The software product can be stored in a computer-readable storage medium, such as ROM/RAM, magnetic disk, compact disk, etc., and include several instructions to cause a computer device (which can be a personal computer, server, network device and the like) to perform the methods described in various embodiments or a part of the embodiments.

Finally, it should be noted that the embodiments above are only for illustrating the technical solutions of the present application, rather than limiting them: although the present application has been described in detail with reference to the foregoing embodiments, those skilled in the art should understand that the technical solutions documented in the preceding embodiments may still be modified, or parts of the technical features thereof may be equivalently substituted; and such modifications or substitutions do not separate the essence of the corresponding technical solutions from the spirit and scope of the technical solutions of the embodiments of the present application.

The invention claimed is:

1. A method for tracking spatial position of an instrument in a three-dimensional scene in real time, the method comprising:
   disposing a first visual marker (e.g., 303) on a scanning device (e.g., 302);
   disposing a second visual marker (e.g., 306) on a scanning area;
   disposing a third visual marker (e.g., 210) on an instrument;
   using the scanning device to scan the scanning area;
   using an optical navigator (e.g., 301) to obtain (e.g., 110) a position of the scanning area relative to the second visual marker based on (i) a spatial position of the first visual marker disposed on the scanning device, (ii) a spatial position of the second visual marker disposed on the scanning area, and (iii) a scanning position of the scanning area obtained by scanning with the scanning device;
   using the optical navigator to register (e.g., 120) the position of the scanning area relative to the second visual marker in the three-dimensional scene to obtain a transformation matrix;
   using the optical navigator to capture (e.g., 210) the spatial position of the second visual marker disposed on the scanning area and a spatial position of a third visual marker disposed on an instrument; and
   using the optical navigator to track (e.g., 220) the spatial position of the instrument in the three-dimensional scene in real time based on (i) the spatial position of the second visual marker, (ii) the spatial position of the third visual marker, and (iii) the transformation matrix.

2. The method of claim 1, wherein using the optical navigator to obtain the position of the scanning area relative to the second visual marker based on the spatial position of the first visual marker disposed on the scanning device, the spatial position of the second visual marker disposed on the scanning area, and the scanning position of the scanning area obtained by scanning with the scanning device comprises:
   obtaining the spatial position of the scanning device based on the spatial position of the first visual marker;
   obtaining the spatial position of the scanning area based on the scanning position of the scanning area and the spatial position of the scanning device; and
   obtaining the position of the scanning area relative to the second visual marker based on the spatial position of the scanning area and the spatial position of the second visual marker.

3. The method of claim 2, wherein the obtaining of the spatial position of the scanning device based on the spatial position of the first visual marker comprises:
   obtaining the spatial position of the scanning device based on the spatial position of the first visual marker and a position of the first visual marker relative to a center of the scanning device.

4. Apparatus for performing the method of claim 3, the apparatus comprising the first, second, and third visual markers, the scanning device, and the optical navigator of claim 3.

5. Apparatus for performing the method of claim 2, the apparatus comprising the first, second, and third visual markers, the scanning device, and the optical navigator of claim 2.

6. The method of claim 1, wherein using the optical navigator to register the position of the scanning area relative to the second visual marker with the three-dimensional scene to obtain the transformation matrix comprises:
   obtaining a position corresponding to the scanning area in the three-dimensional scene based on an iterative closest point algorithm; and
   obtaining the transformation matrix based on the position of the scanning area relative to the second visual marker and the position corresponding to the scanning area in the three-dimensional scene.

7. Apparatus for performing the method of claim 6, the apparatus comprising the first, second, and third visual markers, the scanning device, and the optical navigator of claim 6.

8. The method of claim 1, wherein using the optical navigator to track the position of the surgical instrument in the three-dimensional scene in real time based on the spatial position of the second visual marker, the spatial position of the third visual marker, and a transformation matrix comprises:
   obtaining a spatial position of the instrument based on the spatial position of the third visual marker;
   obtaining a position of the instrument relative to the second visual marker based on the spatial position of the instrument and the spatial position of the second visual marker; and
   updating the position of the instrument in the three-dimensional scene based on the position of the instrument relative to the second visual marker and the transformation matrix.

9. Apparatus for performing the method of claim 8, the apparatus comprising the first, second, and third visual markers, the scanning device, and the optical navigator of claim 8.

10. The method of claim 1, wherein:
    the scanning area is associated with a surgical area (e.g., 303) of a patient; and
    the instrument is a surgical instrument.

11. The method of claim 10, further comprising:
    performing surgery on the patient using the instrument and the three-dimensional scene.

12. The method of claim 11, wherein the surgery is dental implant surgery.

13. Apparatus for performing the method of claim 12, the apparatus comprising the first, second, and third visual markers, the scanning device, and the optical navigator of claim 12.

14. Apparatus for performing the method of claim 11, the apparatus comprising the first, second, and third visual markers, the scanning device, and the optical navigator of claim 11.

15. The method of claim 10, wherein the second visual marker is not implanted into the patient's body.

16. Apparatus for performing the method of claim 15, the apparatus comprising the first, second, and third visual markers, the scanning device, and the optical navigator of claim 15.

17. Apparatus for performing the method of claim 1, the apparatus comprising the first, second, and third visual markers, the scanning device, and the optical navigator of claim 1.

18. Apparatus for performing the method of claim 10, the apparatus comprising the first, second, and third visual markers, the scanning device, and the optical navigator of claim 10.

* * * * *